(12) United States Patent
Garito et al.

(10) Patent No.: US 6,585,791 B1
(45) Date of Patent: Jul. 1, 2003

(54) SMOKE PLUME EVACUATION FILTRATION SYSTEM

(76) Inventors: Jon C. Garito, 1135 Railroad Ave., Hewlett, NY (US) 11557; Alan G. Ellman, 1135 Railroad Ave., Hewlett, NY (US) 11557

( * ) Notice: Subject to any disclaimer, the term of this patent is extended or adjusted under 35 U.S.C. 154(b) by 0 days.

(21) Appl. No.: 10/103,183

(22) Filed: Jan. 29, 2002

(51) Int. Cl.$^7$ .......................... B01D 29/58; B01D 35/30
(52) U.S. Cl. .......................... 55/385.1; 55/472; 55/486; 96/421; 96/422; 604/35
(58) Field of Search ................. 55/385.1, 356, 55/486, 472, 467; 96/421, 422; 95/273; 604/35

(56) References Cited

U.S. PATENT DOCUMENTS

| | | | | |
|---|---|---|---|---|
| 5,288,469 A | * | 2/1994 | Skalla | 422/171 |
| 5,423,779 A | * | 6/1995 | Yeh | 604/317 |
| 5,968,032 A | * | 10/1999 | Sleister | 606/1 |

* cited by examiner

Primary Examiner—Robert A. Hopkins

(57) ABSTRACT

Smoke evacuation apparatus designed to provide safe and efficient filtration and evacuation of smoke plume generated by laser-surgical, electrosurgical, radiosurgical, and electrocautery devices. To ensure capture and removal of the smoke plume, several stages of filtration processes, including a first micro-pre-filter to filter out the most particles and harmful elements at this stage followed by passage of the smoke plume through a main vacuum suction unit and filter to filter out the remaining particles and any odors, are employed. Preferably, the main filter comprises fine charcoal through which the air flows radially which helps remove the odors. In a preferred embodiment, means are provided to monitor the degree of pollution of the main filter to warn users when it is desirable or necessary to replace the main filter. In addition, means are provided to ensure reasonably constant air mass flow to protect against significant clogging of the system which could result in undesirable passage of harmful particles into the environment.

9 Claims, 5 Drawing Sheets

SMOKE PLUME EVACUATION FILTRATION SYSTEM

The invention is directed to apparatus designed to provide safe and efficient filtration of smoke plume generated by laser-surgical, electrosurgical, radiosurgical, cautery, hyfrecators and electrocautery devices.

BACKGROUND OF INVENTION

Surgical smoke evacuation systems are designed to capture the smoke and plume generated during surgical procedures in which there is thermal destruction of tissue or bone. The plume from vaporized tissue contains small particles and gases that could be potentially hazardous. If not evacuated the materials can become airborne and deposit in the respiratory tracts of the surgical team. The type of surgical instruments, the characteristics of tissue, and the surgeon=s technique affect the quantity and characteristics of the smoke plume. A surgical smoke evacuator is in essence a vacuum pump, usually footswitch operated, that incorporates one or more filters to remove particles from the suctioned air-stream at the surgical site. A hose, typically of plastic, disposable or reusable, connects the pump to a disposable or autoclavable wand serving as a nozzle that is usually held about 5 cm. from the tissue to remove smoke generated by the surgical procedure. Because the constraints of some surgical procedures can prevent placement of the nozzle close to the tissue, smoke evacuators should capture smoke effectively at up to 15 cm. Adequate protection from potentially dangerous smoke plume can only be achieved when the plume is successfully captured before it comes into contact with the patient and surgical staff. This smoke entrainment requires that the evacuator airflow change the smoke direction and draw it into the hose via the wand. The ability of a smoke evacuator to collect the surgical plume is highly dependent on three factors; the distance of the wand from the source, the volumetric airflow entering the wand and hose, and the local velocities of the room air.

Successful smoke plume filtration is heavily dependent on several factors. They include:

1. The air flow rate which affects the speed and effectiveness to capture the smoke plume.
2. The extended wand needs to be clog-free to prevent suctioning in any-large objects.
3. The location of the safety wand should allow it to be brought to the close vicinity of the smoke source.
3. An effective micro-pre-filter is needed to have enough area to allow the air flow through and capture the micro particles at the same time.
4. The diameter of the hose affects the speed of the air flow.
5. The air must stay in active charcoal of a main filter long enough to allow the charcoal to act to remove any odors.
6. The motor system must not create or add any particles to the exhausting air.

SUMMARY OF INVENTION

A principal object of the invention is a filtration system that provides a strong air suction flow rate to be able to capture the smoke plumes before they escape.

A further object of the invention is a low cost filtration system that is efficient and reliable.

These objects are achieved in accordance with one aspect of the invention by a filtration system that captures and removes the smoke plume using several stages of filtration processes, including a first micro-pre-filter to filter out the most particles and harmful elements at this stage followed by passage of the smoke plume through a main vacuum suction unit and filter to filter out the remaining particles and any odors. Preferably, the main filter comprises fine charcoal which helps remove the odors.

In a preferred embodiment, means are provided to monitor the degree of pollution of the main filter to warn users when it is desirable or necessary to replace the main filter.

In accordance with another feature of the invention, means are provided to ensure reasonably constant air mass flow to protect against significant clogging of the system which could result in undesirable passage of harmful particles into the environment.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF PREFERRED EMBODIMENTS

Reference is made to a commonly-owned U.S. Pat. No. 6,001,077, whose contents are hereby incorporated by reference. Like the system described in that patent, the surgical smoke evacuation apparatus of the invention employs two independent filters in series in the suction path. The first filter is a viral pre-filter which is capable of filtering microorganisms bigger than 0.02 microns in size. Following the pre-filter is a charcoal filter that efficiently removes odors.

Figure 1:
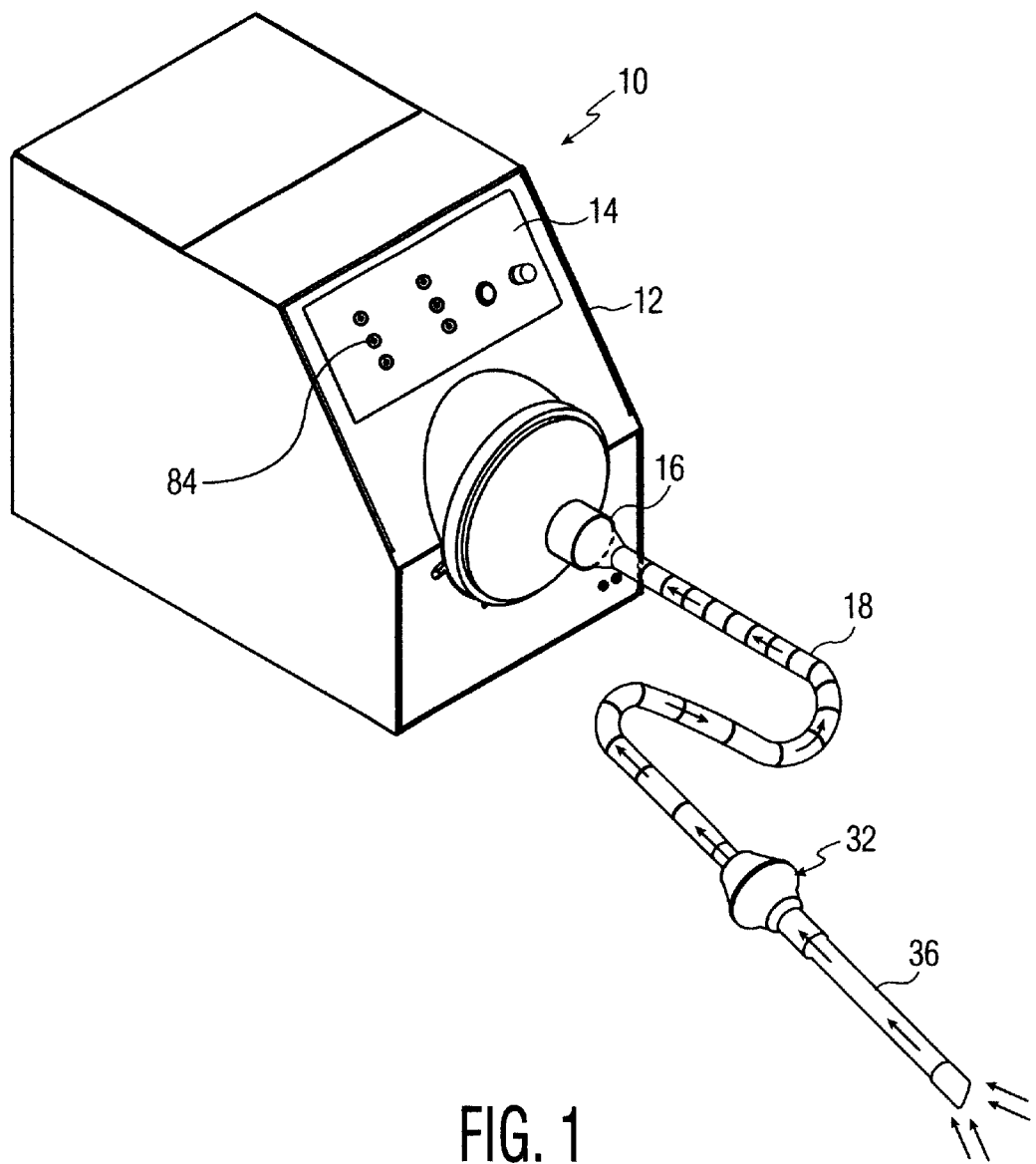
FIG. 1 is a perspective view of one form of a filtration system in accordance with the invention.

A preferred embodiment 10 in accordance with the invention is illustrated in FIG. 1 and comprises a main air-tight (except for an air outlet) housing 12 that provides a control panel and display 14 on the front side and in front an air inlet 16 for receiving a hose connector mounted at the end of a corrugated plastic vacuum hose 18 sufficiently strong to withstand the suction pressure. Inside the housing 12 is provided a brushless DC blower or suction motor 20 available commercially from many suppliers and having an air inlet 22 and an air outlet 24. In operation, an internal 2-stage fan (not shown) develops a suitable suction at its air inlet 22 by discharging a powerful stream of air at its outlet 24. The discharged air exits the housing via a mesh-covered louvered opening 26 at the housing bottom. Standoffs 30 provide easy flow of the exhaust stream to the ambient. The speed of the motor 20 may be controlled in a known manner (more on this below). Typically, the suction generated is inversely proportional to the air flow rate. It is desirable to maintain the air flow rate to ensure that the suction is sufficient to collect any smoke plume pollutants encountered.

The vacuum hose 18 is connected at one end to the housing air inlet 16, and at the opposite end to an external pre-filter 32. Preferably, the pre-filter 32 comprises a viral paper filter capable of filtering micro-organisms exceeding 0.02 microns, and is also available commercially from many suppliers. The viral paper filter is mounted inside a small housing 34 which is not meant to be opened and the housing and assembled filter 32 is easily removed and replaced by any user of the apparatus. To the air inlet side of the pre-filter 32 is connected a wand 36 via its air outlet and with the wand 36 having at its air inlet a mesh tip 38 which is positioned by the practitioner at the site where the smoke plume is generated. The wand is described in more detail in the referenced patent.

Figure 2:
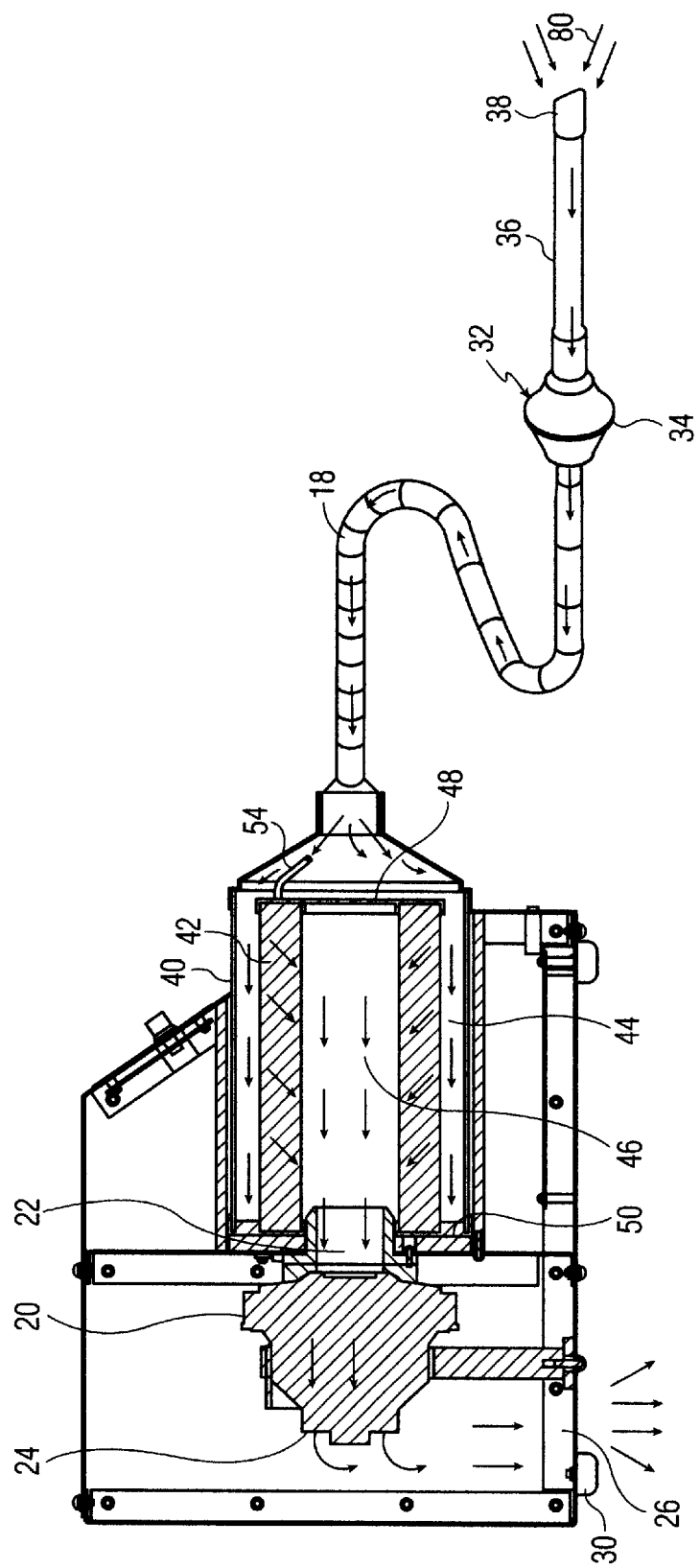
FIG. 2 is a partial perspective cross-sectional view of the system of FIG. 1 illustrating the air flow through the system.
Figure 6:
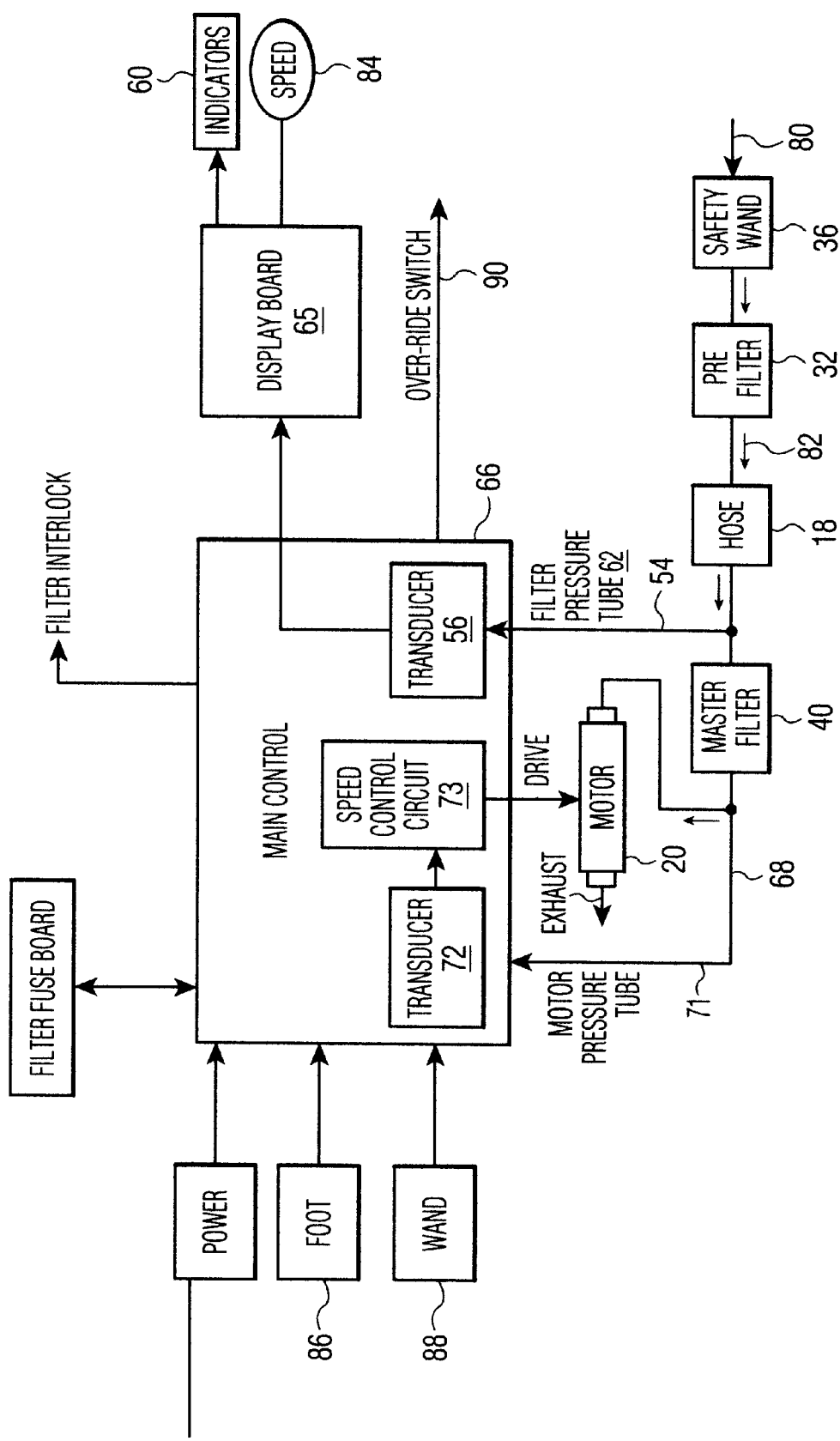
FIG. 6 is a block diagram and schematic of the system showing both electrical and pneumatic relationships.

FIGS. 2 and 6 show by arrows the air flow path. The suction motor 20 creates a large suction that pulls in at the wand 36 end via the mesh 38 outside air 80 including any smoke or plume in the vicinity. Many of the pollutant particles are filtered out by the pre-filter 32, and the suctioned air continues 82 through the hose 18 into the input 16 of the main filter housing 40. The latter houses a replaceable charcoal filter 42 which is in the shape of a cylinder defining within the filter housing 40 an annular cylindrical outer channel 44 and on the charcoal interior an inner cylindrical channel 46. The front end 48 of the filter is sealed off forcing the air to enter the outer channel 44. The rear 50 of the outer channel is also sealed off forcing the air radially through the charcoal walls to the inner channel 46 which communicates with the motor inlet 22. Hence, all the air must flow through the walls of the charcoal filter 42. After passing through the suction motor 20 the filtered air exits via the air output 26. The front of the filter housing 40 can be removed to replace the filter unit 42 when desired.

A feature of the invention is means for indicating or determining when the main filter 40 should be replaced. This is achieved by monitoring the air pressure at the inlet to the main filter 40. In a preferred embodiment, a pressure tube 54 is mounted in the main filter housing 40. The tube inlet 56 is positioned as shown in FIG. 2 to receive a sample of the incoming air which has passed through the pre-filter 32. The air pressure at that point, i.e., at the input to the main filter 40, is an indication of the degree of clogging of the main filter 40. It is a straightforward task to measure that pressure for different levels of filter 40 clogging to determine the degree of clogging of the polluted filter. Essentially this is a calibration task that provides the information for the user to decide when to replace the master filter 40. In general, a conventional pressure transducer 56 (FIG. 6) measuring the air pressure, at that point generates a voltage that is approximately proportional to the pressure increase (over ambient pressure, which is the pressure at the motor outlet). It will be understood that, as the main filter clogs, the air flow reduces which increases the back pressure at the input to the main filter. For example, a higher pressure measurement will provide a higher voltage to trigger a signal that can be used to generate a tone from an annunciator (not shown) and/or turn on an indicator 60 on the front panel display 65, for example a red light, warning the user to replace the master filter. This pressure voltage when calibrated thus determines the degree of pollution within the master filter for replacement. Also, an early warning signal can be obtained by scaling this pressure voltage, and implementing the warning by means of another indicator, for example, signaling a yellow light indicator, to warn the user to have available or procure a stand-by replacement filter. In general, when the air pressure at the sample tube 54 has increased by, say, 40% over the air pressure measured when a clean filter is present is a good time to replace the main filter to avoid the risk of incomplete removal of all possible pollutants.

Figure 3:
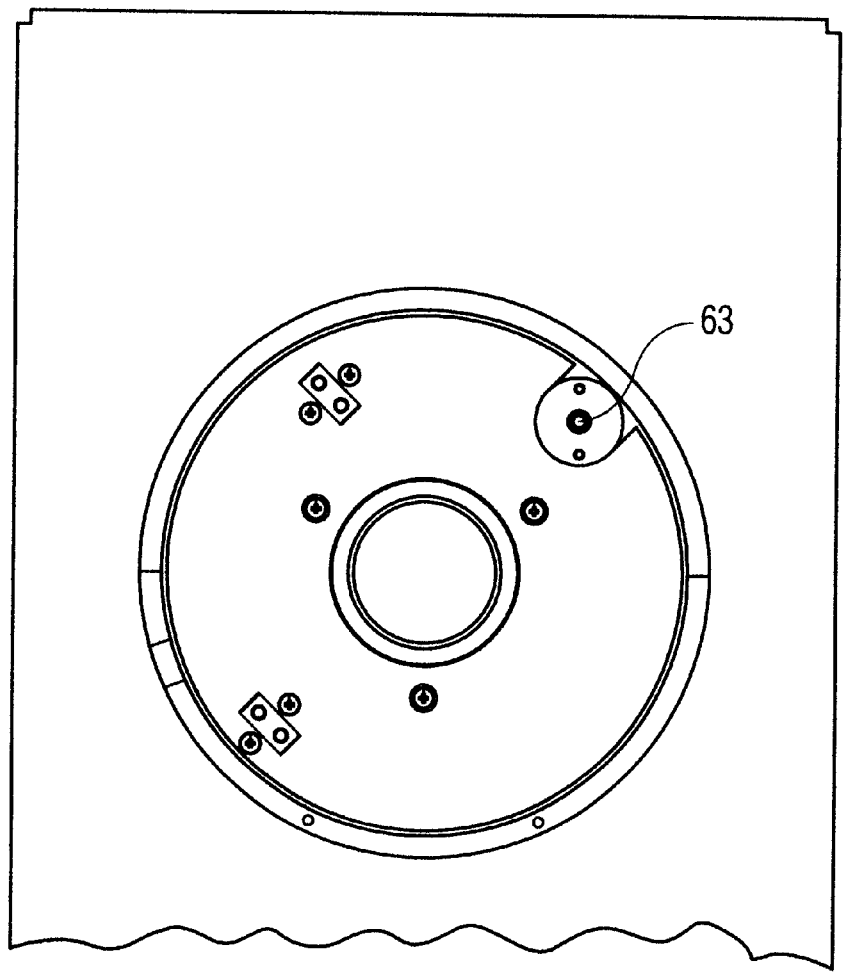
FIG. 3 is a rear view of the system housing with the back cover removed.

The transducer itself, not shown in FIG. 2 but in FIG. 6, may be located inside the filter housing 40 and an electrical wire used to connect the transducer to a control circuit 66 on a PCB within the evacuator housing 12. Alternatively, the air pressure pipe 54 can be extended through the outer channel 44 to the rear of the filter housing, and a flexible tube 62 connected to the pipe via a nipple 63 at the rear of the filter (see FIG. 3) can be used to convey the air pressure to the transducer 56 on the PCB.

Figure 4:
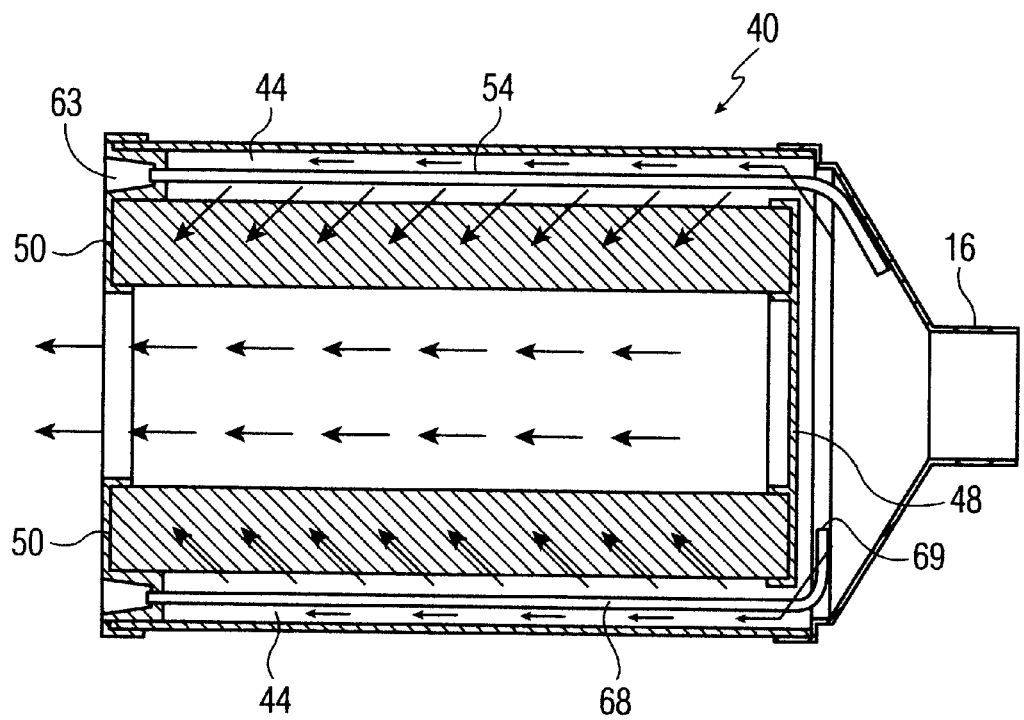
FIG. 4 is an enlarged cross-sectional view of the main filter taken along its center axis in the plane of the drawing.
Figure 5:
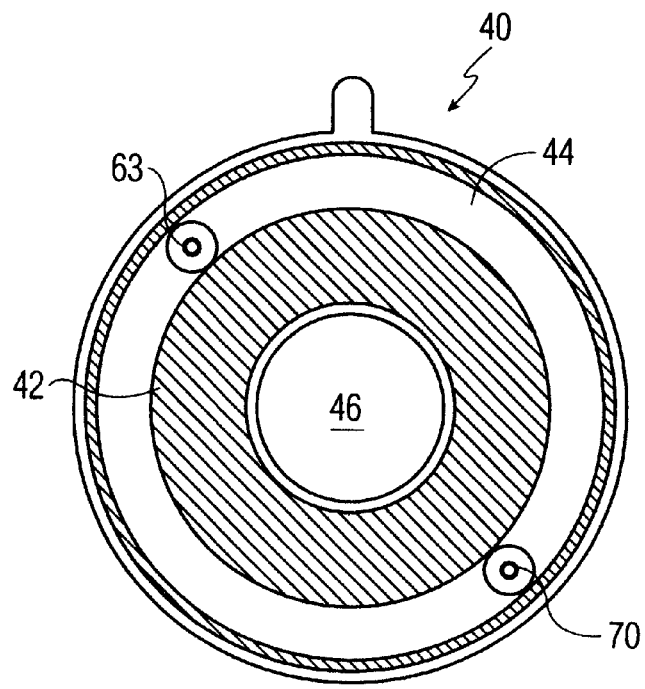
FIG. 5 is an enlarged cross-sectional view of the main filter taken along a plane perpendicular to the plane of the drawing.

As an alternative, as illustrated in FIG. 4, the air tube 54 can travel through the outer channel 44 to the outlet 63 for carrying the pressure at the main filter entrance to the pressure transducer 56.

As a further feature of the invention, means are provided to control the motor speed. This also can be accomplished with a second air tube 68 travelling through the outer channel 44 and having an inlet 69 at the main filter entrance and an outlet 70 for carrying the pressure via a flexible air hose 71 at the main filter exit to a second pressure transducer 72 in the main control 66. Alternatively, the first and second air tubes 54, 68 can be combined into a single tube.

The second pressure transducer 72 measures the pressure difference across the motor 20, as the motor releases air into the ambient atmosphere, the exit pressure would be close to atmospheric pressure though, perhaps, a small discrepancy is expected. The pressure increasing rate is an almost linear decreasing offset function of the air mass flow. The voltage generated by the second pressure transducer 72 is utilized to control the motor speed in a conventional manner 73 for maintaining a constant air mass flow rate through the system. This ensures that collection of pollutants is optimized. Rapid drop of the air flow rate can be used to trigger a signal to disable the motor for it means an undesirable clogging in the air flow path that is interfering with the pollution collection. The user at that point should discontinue or interrupt the procedure to determine the clogging point and to fix it.

FIG. 6 shows other elements of the control system which are straightforward for the person of ordinary skill in the art to implement, so it is deemed unnecessary to supply more than the minimum details. FIG. 6 shows not only electrical components and their relationships, but also pneumatic relationships by the arrows indicating air flow as well as the signal flow. For example, an indicator 84 on the board can display speed, foot 86 represents a foot switch for activating the system, the wand symbol 88 underneath represents a possible on-off switch on the wand, and the remaining items are readily understood from their label. The main control system can be readily implemented by a conventional microcontroller suitably programmed to respond to the various inputs and to activate various outputs as required, or by a hard-wired digital circuit to supply the functions described.

In summary, the filtration system of the invention provides a strong air suction flow rate able to capture the smoke plume before it escapes. The extended wand will easily reach to the surgical site. The in-line micro-filter provides the first defense to capture harmful bio-particles and prevent large particles from getting into the filtration system, as well as to keep clog away from the filter system and simultaneously maintain the required air flow rate. The large charcoal filter and the described radial flow path provides room and time for the polluted air to react with the active charcoal to remove any odors, leaving exhausting air as fresh as the unpolluted room air. In addition, the system provides high suction and high flow rate. The safety screen 38 at the wand entrance keeps large tissue particles out of the system. The external filter 32 in addition to trapping microorganisms removes casual fluid. This external filter 32 is a single use filter, and can be easily installed or replaced for filter changes as it is completely enclosed in a plastic compartment to prevent health care personnel from potential contamination.

The master filter 40 functions to absorb and purify the toxic gases and odors produced by the burning tissue. It accomplishes this with high quality activated carbon. The pressure sensors for monitoring the air flow path through the master filter achieve the highest efficiency and ensure its function. The filtration system can also be monitored by an operational timer as well as air flow pressure sensors. When it has been operated for a certain set period and/or the air flow pressure reaches a certain threshold level, the filtration system will trigger a warning light to tell the user that replacement of the master filter is in order. The filtration system will re-set its pressure level and timing counter system upon replacing the master filter.

While, for best protection, when it is time to replace the master filter, the filtration system will stop functioning after the warning light is ON. However, in the event of an emergency, an override switch 90 is provided to allow the system to continue functioning. The filtration system may continue its service for the last time as long as its power supply is not interrupted. This can also be implemented by incorporating a one-time use fuse on the master filter which allows only one use when the override switch is activated.

The motor speed control is easily implemented with a known integrated circuit to control the motor speed and its function.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. Apparatus for smoke plume evacuation arising from operation of laser-surgical, electrosurgical, radiosurgical, and electrocautery devices, comprising:

a) a housing having an air inlet and an air outlet,
    b) a removable odor-removing main filter having an air inlet and an air outlet inside the housing, the main filter comprising an annular odor-removing member defining an outer channel and an inner channel connected for air flow only through the odor-removing member, the main filter air inlet being connected to one of the outer and inner channels, the main filter air outlet being connected to the other of the outer and inner channels, whereby incoming air must flow through the odor-removing member to reach the main filter air outlet,
    c) means connecting the main filter air inlet to the housing air inlet,
    d) motor means in the housing for forcing air to flow between a motor air inlet and a motor air outlet establishing a suction at the motor air inlet,
    e) means connecting the motor air outlet to the housing air outlet,
    f) means connecting the motor air inlet to the main filter air outlet,
    g) a vacuum hose connected to the housing air inlet whereby suction is available at the hose when the apparatus is activated,
    h) an external viral pre-filter assembly removably connected to the vacuum hose in series with air flow through the hose,
    i) a wand connected to the viral filter assembly,
    j) first means for monitoring the air pressure main filter inlet,
    k) second means for monitoring the air pressure at the main filter inlet.

2. Apparatus as claimed in claim 1, wherein the main filter comprises a cylindrical housing and the odor-removing member is configured as a hollow cylindrical member mounted within the filter housing, the outer channel being defined by the outside surface of the odor-removing member and the inside surface of the housing, and the inner channel being defined by the inside surface of the odor-removing member.

3. Apparatus as claimed in claim 2, wherein the main filter inlet is connected to the main filter outer channel, and the main filter outlet is connected to the main filter inner channel, whereby the air flow through the odor-removing member is radially from the outer channel to the inner channel.

4. Apparatus as claimed in claim 1, wherein the first means for monitoring the air pressure comprises an air tube mounted in the main filter and having an air inlet at the air inlet of the main filter.

5. Apparatus as claimed in claim 4, further comprising a first pressure transducer connected to the first means for monitoring the air pressure for generating an electrical signal indicative of restrictions on the air flow through the main filter.

6. Apparatus as claimed in claimed 5, further comprising means connected to the first pressure transducer for indicating increased air pressure at the main filter inlet.

7. Apparatus as claimed in claim 1, wherein the second means for monitoring the air pressure comprises an air tube mounted in the main filter and having an air inlet at the air inlet of the main filter.

8. Apparatus as claimed in claim 7, further comprising a second pressure transducer connected to the second means for monitoring the air pressure for generating an electrical signal indicative of a reduction in the air flow rate through the main filter.

9. Apparatus as claimed in claim 8, further comprising means connected to the second pressure transducer for controlling the speed of the motor.

\* \* \* \* \*